United States Patent
Xu et al.

(10) Patent No.: US 10,128,014 B2
(45) Date of Patent: Nov. 13, 2018

(54) CONTROLLING MOVEMENT OF CARRIAGE OF MULTI-LEAF COLLIMATOR

(71) Applicant: Shenyang Neusoft Medical Systems Co., Ltd., Shenyang (CN)

(72) Inventors: Xinghu Xu, Shenyang (CN); Meng Chai, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 0 days.

(21) Appl. No.: 15/642,091

(22) Filed: Jul. 5, 2017

(65) Prior Publication Data

US 2018/0012676 A1  Jan. 11, 2018

(30) Foreign Application Priority Data

Jul. 6, 2016  (CN) .......................... 2016 1 0529311
Jun. 28, 2017  (CN) .......................... 2017 1 0508075

(51) Int. Cl.
*G21K 1/04* (2006.01)
*A61N 5/10* (2006.01)

(52) U.S. Cl.
CPC .......... *G21K 1/046* (2013.01); *A61N 5/1036* (2013.01); *A61N 5/1045* (2013.01); *A61N 5/1065* (2013.01)

(58) Field of Classification Search
CPC .... G21K 1/046; A61N 5/1036; A61N 5/1045; A61N 5/1065
See application file for complete search history.

(56) References Cited

U.S. PATENT DOCUMENTS

2006/0256915 A1   11/2006  Otto et al.
2011/0049396 A1*  3/2011   Furth .................. A61N 5/1042
                                                         250/505.1

FOREIGN PATENT DOCUMENTS

WO   2005018742 A1   3/2005
WO   2012171538 A1   12/2012

OTHER PUBLICATIONS

European Patent Office: Extended European Search Report mailed in corresponding European Patent Application No. 7179966.1 dated Nov. 24, 2017 (7 pages).

\* cited by examiner

*Primary Examiner* — Eliza Osenbaugh-Stewart
(74) *Attorney, Agent, or Firm* — Fish & Richardson P.C.

(57) ABSTRACT

Methods and devices for controlling movement of a carriage of a multi-leaf collimator are provided. In one aspect, a method includes obtaining a desired position of each of a set of leaves on the carriage in each of a plurality of segments from a field, determining an allowable moving range set of the carriage according to the desired position, the allowable moving range set including a respective allowable moving range of the carriage in each of the segments, determining a respective position of the carriage in each of the segments according to the allowable moving range set, and controlling the movement of the carriage according to the determined positions of the carriage in the segments.

16 Claims, 6 Drawing Sheets

CONTROLLING MOVEMENT OF CARRIAGE OF MULTI-LEAF COLLIMATOR

CROSS REFERENCE TO RELATED APPLICATIONS

This application claims priority to Chinese Patent Application No. 201610529311.6, filed on Jul. 6, 2016 and Chinese Patent Application No. 201710508075.4, filed on Jun. 28, 2017, the entire contents of which are incorporated herein by reference.

TECHNICAL FIELD

The present disclosure is related to controlling movement of a carriage of a multi-leaf collimator.

BACKGROUND

Radiation therapy is one of the conventional means of treating tumour. In radiation therapy, a radiation range of rays must be limited. The radiation range of rays may be called a radiation field, which makes the rays only kill a tumour tissue and try to protect normal tissues around the tumour tissue. Currently, a multi-leaf collimator (MLC) may be used to control the radiation field of rays so as to achieve a precise treatment.

The multi-leaf collimator is an important component of a radiotherapy apparatus and may be installed in a treatment machine head of the radiotherapy apparatus. Main components of the multi-leaf collimator may include two symmetrically-distributed sets of leaves. Each of the leaves may be driven by a separate motor, respectively, thereby forming different radiation fields.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods and devices for controlling movement of a carriage of a multi-leaf collimator, which can decrease a number of movements and/or moving distance for the carriage, thereby decreasing a position error caused by the movements and ensuring an accuracy of a formed radiation field.

In general, one innovative aspect of the subject matter described in the present disclosure can be embodied in methods that include the actions of obtaining a desired position of each of a set of leaves on the carriage in each of a plurality of segments from a field; determining an allowable moving range set of the carriage according to the desired position, where the allowable moving range set includes a respective allowable moving range of the carriage in each of the segments; determining a respective position of the carriage in each of the segments according to the allowable moving range set; and controlling the movement of the carriage according to the determined respective positions of the carriage in the segments.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. For example, determining the respective position of the carriage in each of the segments according to the allowable moving range set may further include: determining a reference point according to the allowable moving range set; and taking a position closest to the reference point in each of the allowable moving ranges as the respective position of the carriage in the corresponding segment. In some examples, determining the reference point according to the allowable moving range set may include: calculating, for each of a plurality of candidate reference points, a respective total moving distance representing a sum of absolute values of distances for the carriage from the candidate reference point to each of the allowable moving ranges in the allowable moving range set; and determining the candidate reference point having a minimum total moving distance among the determined respective total moving distances to be the reference point. In some examples, the method may further include: determining a distance for the carriage from the candidate reference point to each of the allowable moving ranges by determining the distance to be zero if the candidate reference point is within an allowable moving range, and determining the distance to be from the candidate reference point to a closest endpoint of an allowable moving range if the candidate reference point is out of the allowable moving range.

In some implementations, determining the respective position of the carriage in each of the segments according to the allowable moving range set may include: taking an endpoint of each of the allowable moving ranges in the allowable moving range set as a hypothetical reference point; generating, for each of the hypothetical reference points, a corresponding position sequence including a respective position point closest to the hypothetical reference point in each of the allowable moving ranges; calculating, for each of the hypothetical reference points, a respective total moving distance representing a sum of absolute values of distances for the carriage from the hypothetical reference point to each of the position points in the corresponding position sequence; determining the hypothetical reference point with a minimum total moving distance among the calculated respective total moving distances to be a reference point of the carriage; and determining the respective position of the carriage in each of the segments according to a position sequence corresponding to the reference point.

In some implementations, the method may further include: determining whether there is an intersection between each of the allowable moving ranges in the allowable moving range set; in response to determining that there is an intersection between each of the allowable moving ranges, taking a position point closest to an initial position of the carriage in the intersection as a reference point, and determining the reference point as the position of the carriage in each of the segments; and in response to determining that there is no intersection between each of the allowable moving ranges, determining the respective position of the carriage in each of the segments according to the allowable moving range set.

In some implementations, determining the respective position of the carriage in each of the segments according to the allowable moving range set may include determining whether a current position of the carriage is located within an allowable moving range of a next segment in the allowable moving range set; in response to determining that the current position of the carriage is located within the allowable moving range of the next segment, determining the current position to be the respective position of the carriage in the next segment; and in response to determining that the current position of the carriage is out of the allowable moving range of the next segment, determining a position closest to the current position in the allowable moving range of the next segment is to be the respective position of the carriage in the next segment.

In some implementations, obtaining the desired position of each of the set of leaves on the carriage in each of the plurality of segments from the field may include: determining the desired position of each of the set of leaves on the carriage in each of the segments from the field based on a treatment prescription, wherein the treatment prescription includes a treatment plan corresponding to the field, and each of the segments corresponds to a radiation field formed when each of the set of leaves is located at the desired position at a respective time of the treatment plan.

In some implementations, determining the allowable moving range set of the carriage may include: determining, for each of the segments, endpoints of the respective allowable moving range of the carriage, wherein the endpoints represent minimum and maximum positions of the carriage when the leaves are in the desired positions in the segment and an end of the carriage is aligned with ends of the leaves.

In some examples, controlling the movement of the carriage may include: jointly moving the carriage and the set of leaves on the carriage.

Another innovative aspect of the subject matter described in the present disclosure can be embodied in a device for controlling movement of a carriage of a multi-leaf collimator. The device includes one or more processors and a non-transitory machine-readable storage medium having instructions stored thereon which, when executed by the one or more processors, cause the one or more processors to perform operations including: obtaining a desired position of each of a set of leaves on the carriage in each of a plurality of segments from a field; determining an allowable moving range set of the carriage according to the desired position, where the allowable moving range set includes a respective allowable moving range of the carriage in each of the segments; determining a respective position of the carriage in each of the segments according to the allowable moving range set; and controlling the movement of the carriage according to the determined respective positions of the carriage in the segments.

In some examples, determining the respective position of the carriage in each of the segments according to the allowable moving range set may include: determining a reference point according to the allowable moving range set; and taking a position closest to the reference point in each of the allowable moving ranges as the respective position of the carriage in the corresponding segment. In some examples, determining the reference point according to the allowable moving range set may include: calculating, for each of a plurality of candidate reference points, a respective total moving distance representing a sum of absolute values of distances for the carriage from the candidate reference point to each of the allowable moving ranges in the allowable moving range set; and determining the candidate reference point having a minimum total moving distance among the determined respective total moving distances to be the reference point. In some examples, the operations may further include determining a distance for the carriage from the candidate reference point to each of the allowable moving ranges by determining the distance to be zero if the candidate reference point is within an allowable moving range, and determining the distance to be from the candidate reference point to a closest endpoint of an allowable moving range if the candidate reference point is out of the allowable moving range.

In some implementations, determining the respective position of the carriage in each of the segments according to the allowable moving range set may include: taking an endpoint of each of the allowable moving ranges in the allowable moving range set as a hypothetical reference point; generating, for each of the hypothetical reference points, a corresponding position sequence including a respective position point closest to the hypothetical reference point in each of the allowable moving ranges; calculating, for each of the hypothetical reference points, a respective total moving distance representing a sum of absolute values of distances for the carriage from the hypothetical reference point to each of the position points in the corresponding position sequence; determining the hypothetical reference point with a minimum total moving distance among the calculated respective total moving distances to be a reference point of the carriage; and determining the respective position of the carriage in each of the segments according to a position sequence corresponding to the reference point.

In some implementations, the operations may further include: determining whether there is an intersection between each of the allowable moving ranges in the allowable moving range set; in response to determining that there is an intersection between each of the allowable moving ranges, taking a position point closest to an initial position of the carriage in the intersection as a reference point, and determining the reference point as the position of the carriage in each of the segments; and in response to determining that there is no intersection between each of the allowable moving ranges, determining the respective position of the carriage in each of the segments according to the allowable moving range set.

In some implementations, determining the respective position of the carriage in each of the segments according to the allowable moving range set may further include: determining whether a current position of the carriage is located within an allowable moving range of a next segment in the allowable moving range set, in response to determining that the current position of the carriage is located within the allowable moving range of the next segment, determining the current position to be the respective position of the carriage in the next segment; and in response to determining that the current position of the carriage is out of the allowable moving range of the next segment, determining a position closest to the current position in the allowable moving range of the next segment is to be the respective position of the carriage in the next segment.

In some implementations, obtaining the desired position of each of the set of leaves on the carriage in each of the plurality of segments from the field may further include determining the desired position of each of the set of leaves on the carriage in each of the segments from the field based on a treatment prescription, wherein the treatment prescription includes a treatment plan corresponding to the field, and each of the segments corresponds to a radiation field formed when each of the set of leaves is located at the desired position at a respective time of the treatment plan.

In some implementations, determining the allowable moving range set of the carriage may include: determining, for each of the segments, endpoints of the respective allowable moving range of the carriage, wherein the endpoints represent minimum and maximum positions of the carriage when the leaves are in the desired positions in the segment and an end of the carriage is aligned with ends of the leaves.

In some examples, controlling the movement of the carriage may include jointly moving the carriage and the set of leaves on the carriage.

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Combined with the drawings in examples of the present disclosure, the following will describe the technical solution in examples of the present disclosure clearly and completely. It is apparent that the described examples are merely part of the examples of the present application, and not all examples. Based on examples of the present disclosure, all other examples obtained by those of ordinary skill in the art without making creative work are within the scope of the present disclosure.

There can be two main methods of controlling movement of the multi-leaf collimator. The first method can be to directly control the movement of each of the leaves. For example, a plurality of motors may be configured to directly drive each of the leaves, respectively, in such a way that each of the leaves is moved to a desired position. The second method can be to use different motors to control the movement of the carriage and the movement of the leaves, respectively. For example, two sets of leaves can be disposed on two carriages, respectively. On one hand, two motors may be respectively configured to drive the two carriages; on the other hand, other motors may be configured to drive each of the leaves, respectively. The second method can speed up the movement of the leaves and increase the allowable moving distance of the leaves, thereby increasing the formation area and the feasibility of formation for the radiation field.

During a treatment process, different radiation fields can be formed. For the second method, during the process of moving from a current radiation field to a next radiation field, a position of each of the leaves may be related to a position of the carriage. The position of the carriage may be related to an accuracy of the movement of each of the leaves, which may affect an accuracy of the formed radiation field. Therefore, how to determine the position of the carriage is one of the key points to form an accurate radiation field.

Implementations of the present disclosure provide a method of controlling movement of a carriage of a multi-leaf collimator. The multi-leaf collimator can be a mechanical motion component used in radiotherapy for producing a conformal radiation field. The multi-leaf collimator can be a multi-leaf collimator having two carriages, where two sets of symmetrically-distributed leaves can be respectively disposed on the two carriages and each carriage can be driven by a separate motor and each of the leaves on the two carriages can be driven by their respective motors.

Figure 1:
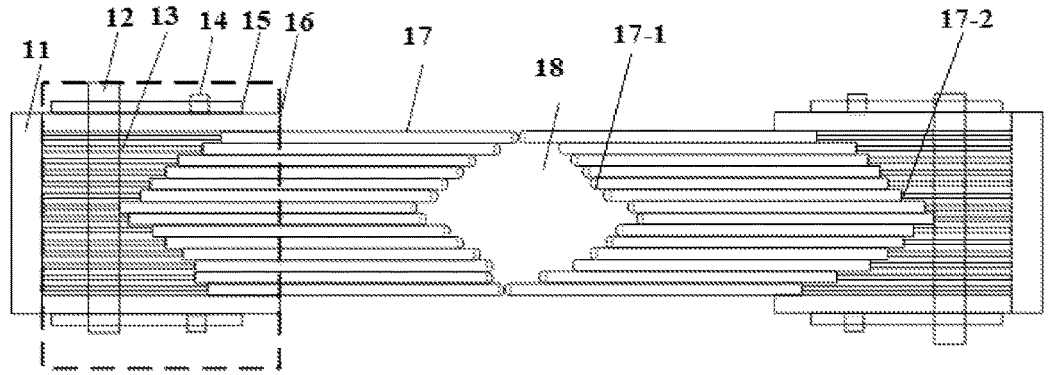
FIG. 1 is a top view architectural diagram of a multi-leaf collimator according to one or more examples of the present disclosure.

A material of the leaves can include metal tungsten. Because rays cannot easily penetrate the metal tungsten, a lower part of areas covered by the leaves may not be radiated by rays. The two sets of leaves may be symmetrically distributed and each of the leaves may be driven by the corresponding motor to a respective desired position. An area 18 not covered by the leaves may be formed between ends of the two sets of leaves (as illustrated in FIG. 1). Rays may pass through the area 18 not covered by the leaves. The area 18 not covered by the leaves may be called a radiation field. In this way, a suitable shape of a radiation field may be formed by using each motor to drive each of the leaves.

During a radiotherapy process, a treatment project may include a plurality of treatment stages, and each treatment stage may adopt a different treatment plan. In each treatment plan, different radiation fields may be formed by the leaves in different times based on a cumulative dose of beam. Hereinafter, a treatment plan may be called a field, and a radiation field in the field may be called a segment.

In a field, different segments may be formed by driving each of the leaves to make it locate at different positions. For the present disclosure, a method of jointly moving the carriage and the corresponding leaves may be adopted, in such a way that each of the leaves may be located at the desired position. This method enables to appropriately shorten the length of the leaves and reduce the volume of the leaves, thereby reducing manufacturing cost of the leaves. In addition, this method further enables to appropriately reduce moving distance of each of the leaves, thereby reducing requirement for driving ability of the leaves.

FIG. 1 is a top view architectural diagram of a multi-leaf collimator according to one or more examples of the present disclosure. The multi-leaf collimator includes two parts each including a set of leaves 17 and a carriage 16, a substrate 12, a leaf screw 13, a carriage screw 15, a screw hole 14, and a plurality of motors 11. The substrate 12 is configured to fix the carriage 16. The carriage 16 may be connected to the carriage screw 15 that is engaged with the screw hole 14. A motor 11 for the carriage 16 can drive the carriage screw 15, which in turn causes the carriage 16 to move in a straight line. Two sets of leaves 17 may be disposed on the two carriages 16, respectively, where these two sets of leaves 17 are symmetrically distributed. Each of the leaves 17 may be driven by a separate motor 11. Each leaf 17 may be connected to a leaf screw 13, and the leaf screw 13 may be driven by the motor for the leaf 17 to thereby cause the leaf 17 to move in a straight line. The set of leaves 17 can be moved jointly together with the carriage 16 and each leaf 17 can also be individually moved by the motor 11 in relative to the carriage 16.

In some examples, the carriage 16 is configured to drive the leaf to move concurrently. In some examples, the carriage 16 is configured to withdraw the leaf. The leaf 17 can be withdrawn until a front end 17-1 of the leaf 17 is aligned with a front end of the carriage 16. The leaf 17 may be extended until a rear end 17-2 of the leaf 17 is aligned with the front end of the carriage 16. Note that, the front end 17-1 of the leaf 17 on one set of leaves refers to the end of the leaf 17 opposite to a corresponding end of a leaf of the other set of leaves. The rear end 17-2 of the leaf 17 refers to the other end that are opposite to the front end of the leaf 17. The front end of the carriage 16 refers to the end of the carriage 16 opposite to a corresponding end of the other carriage 16.

The multi-leaf collimator described in detail above is merely an example for the purpose of facilitating a better understanding of the method of controlling movement of a carriage of a multi-leaf collimator, and the structure of the multi-leaf collimator having carriages is not particularly limited in the present disclosure. Any suitable structure may be adopted such that both the carriages and the leaves are moved to make the leaves locate at the desired positions.

Figure 2:
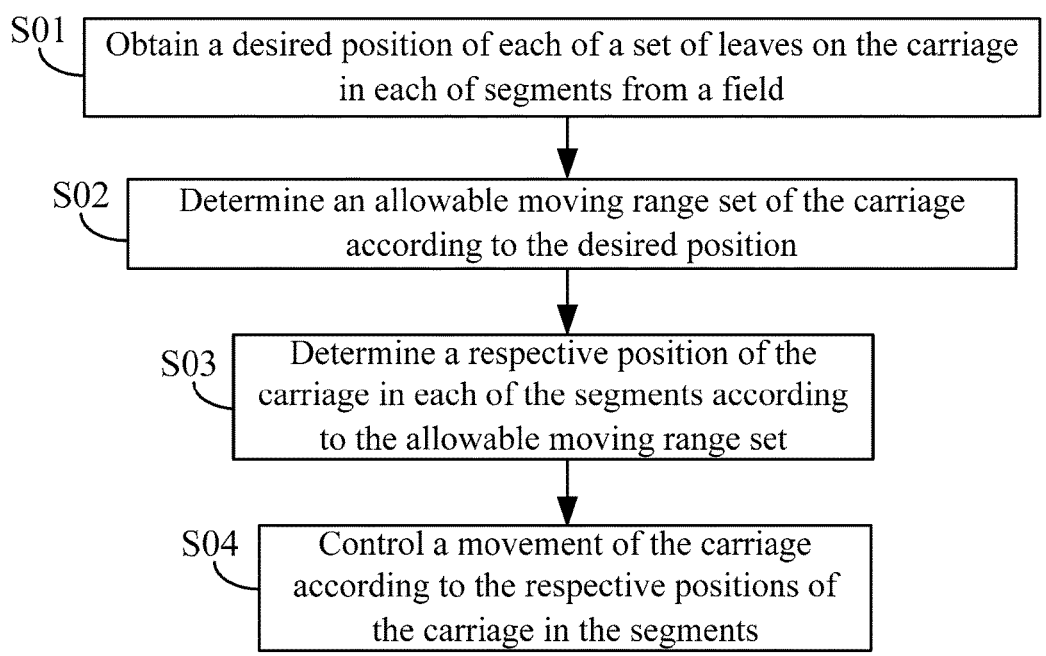
FIG. 2 is a flowchart illustrating a method of controlling movement of a carriage of a multi-leaf collimator according to one or more examples of the present disclosure.

For the above-described multi-leaf collimator, the method of controlling movement of a carriage of the multi-leaf collimator is provided in the present disclosure. FIG. 2 is a flowchart illustrating the method of controlling movement of the carriage of the multi-leaf collimator according to one or more examples of the present disclosure. The method can include a process having steps S01-S04.

At step S01, a desired position of each of a set of leaves on the carriage in each of segments from a field is obtained.

At step S02, an allowable moving range set of the carriage is determined according to the desired position, where the allowable moving range set includes one or more sub-sets and each sub-set is an allowable moving range of the carriage in each of the segments.

At step S03, a respective position of the carriage in each of the segments is determined according to the allowable moving range set.

At step S04, a movement of the carriage is controlled according to the respective positions of the carriage in the segments.

The multi-leaf collimator may include two symmetrically-distributed carriages. For each of the carriages, the above method may be used to control its movement. The steps S01-S04 may be simultaneously performed on the two carriages, or the steps S01-S04 may be respectively performed on the two carriages, and the present disclosure is not limited thereto. The allowable moving range set may refer to a set of allowable moving ranges of the carriage in each of the segments, which may include a plurality of sub-sets and each of the sub-sets may correspond to an allowable moving range of the carriage in a segment.

In this method, the allowable moving range set of the carriage may be determined according to the desired position of each of the set of leaves on the carriage in each of the segments included in a field corresponding to a treatment plan, and the position of the carriage in each of the segments may be determined according to the allowable moving range set. This method may decrease a number of movements and/or moving distance for the carriage, thereby decreasing the position error caused by the movements and ensuring the accuracy of the formed radiation field.

To better understand technical schemes and technical effects of the present disclosure, the following detailed description will be made with reference to specific examples.

Example 1

Figure 3A:
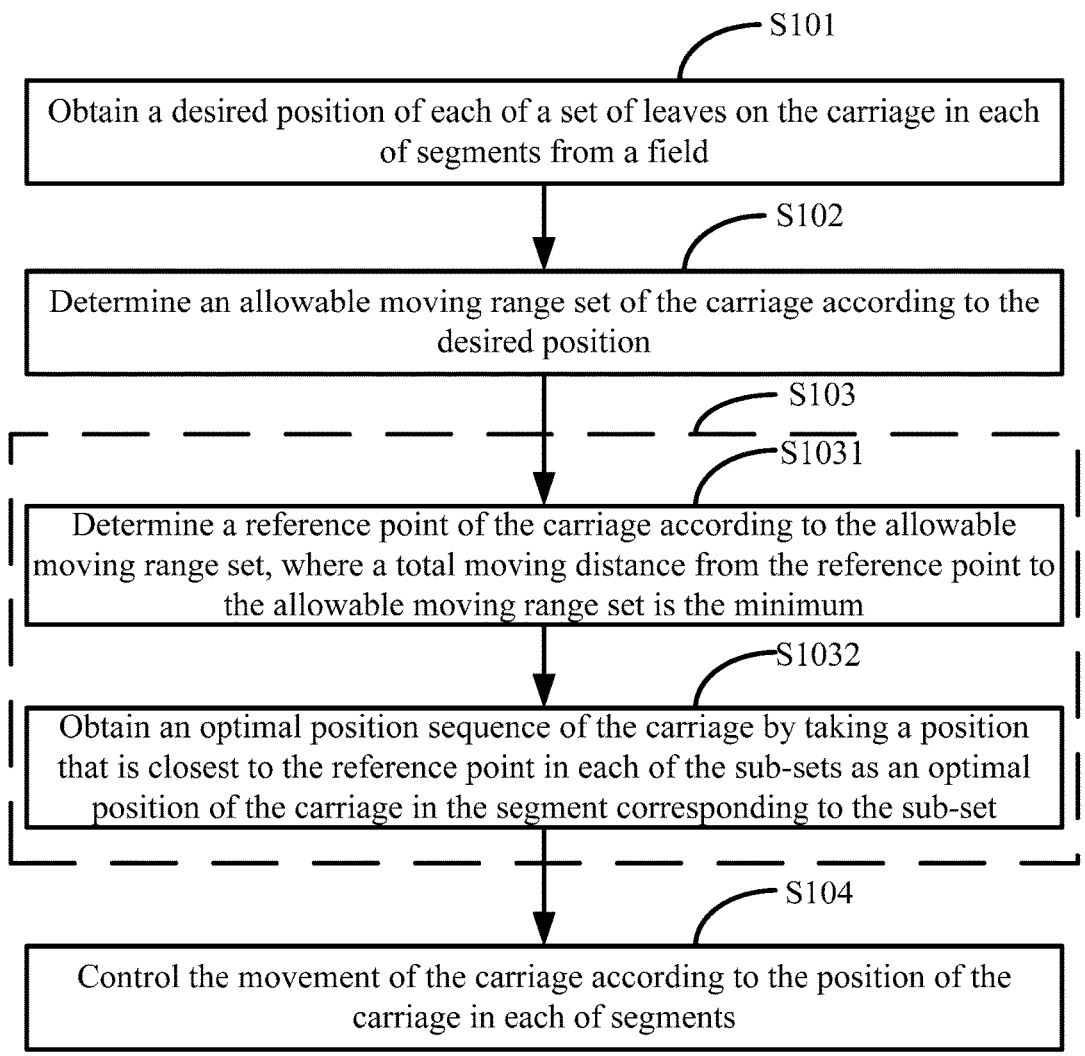
FIGS. 3A-3B show flowcharts illustrating a method of controlling movement of a carriage of a multi-leaf collimator according to Example 1 of the present disclosure.
Figure 3B:
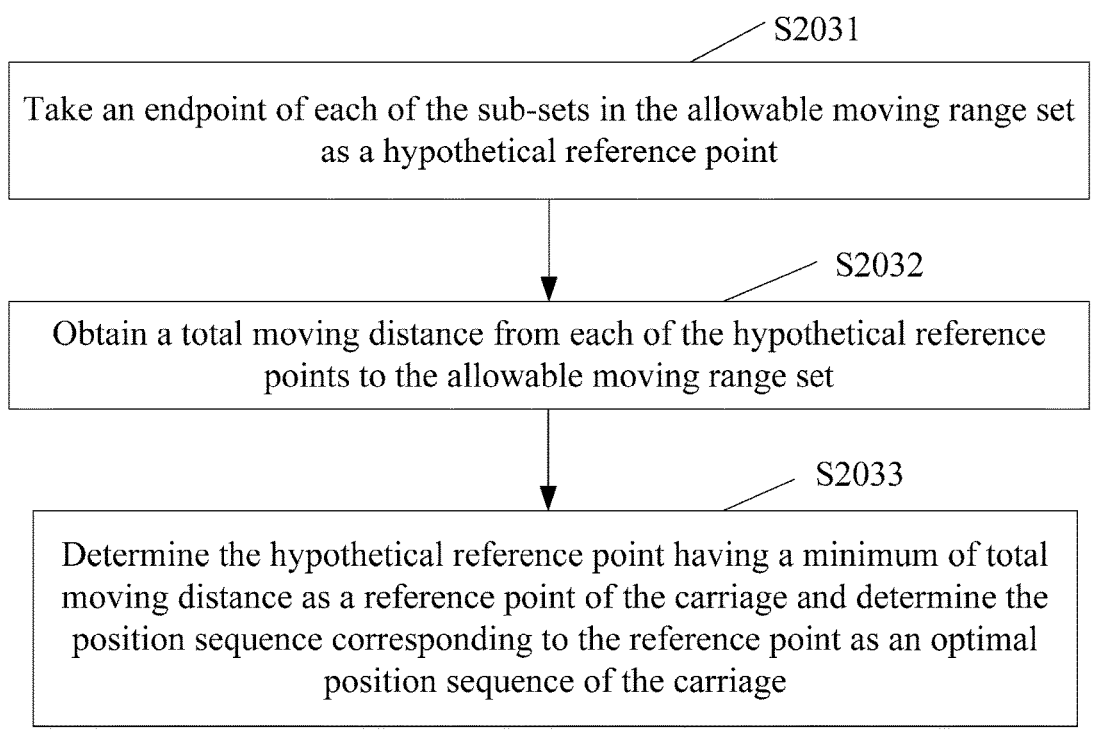

FIGS. 3A-3B are flowcharts illustrating a method of controlling movement of a carriage of a multi-leaf collimator according to Example 1 of the present disclosure. The method includes a process having multiple steps as shown in FIGS. 3A-3B.

At step S101, a desired position of each of a set of leaves on the carriage in each of segments from a field is obtained.

In the field (e.g., a treatment plan), at different times, the leaves may show different shapes according to different doses of beam, thereby forming a segment. For example, in different segments, a radiation field of a desired shape may be formed when each of the leaves is located at the desired position.

In some implementations, the desired position of each leaf in each of the segments is obtained from a treatment prescription. The treatment prescription can include patient information, a treatment plan, and the desired position of each leaf in each of the segments. The treatment prescription may be stored in a text form. The desired position can be a predetermined position. The desired position of each leaf in each of the segments can be obtained from the treatment prescription, where the desired position may be coordinate information or any other information that may represent the leaf position. In some cases, the desired position of each leaf on one of the two carriages in each of segments can be obtained first. In some cases, the desired position of each leaf on the two carriages in each of segments can be obtained simultaneously.

In some examples, an examination of the information in the treatment prescription is performed first. If the information in the treatment prescription is incorrect, the process returns to modify the treatment prescription until that the information in the treatment prescription is correct, and then the desired position of each leaf in each of segments may be extracted from the treatment prescription.

At step S102, an allowable moving range set of the carriage is determined according to the desired position.

At this step, the allowable moving range set of the carriage may be determined according to the desired position of each of the leaves, e.g., possible moving allowable ranges of the carriage in each of the segments may be determined. The allowable moving range set may include one or more sub-sets, and each of the sub-sets may be an allowable moving range of the carriage in a corresponding segment. For an allowable moving range set $\{X_i\}$ of the carriage, $A_i \leq X_i \leq B_i$, where i is from 1 to k1, and k1 represents a number of the segments, $X_i$ corresponds to an allowable moving range of the carriage in an i-th segment, and $A_i$ and $B_i$ respectively represent a minimum position and a maximum position of the carriage in the i-th segment.

The allowable moving range set may include a plurality of sub-sets and each of the sub-sets may refer to an allowable moving range of the carriage in a corresponding segment. In each of the segments, a radiation field of a desired shape may be formed when each of the leaves is located at the desired position, thereby facilitating the passage of rays. The carriage may include an allowable moving range when each of the leaves in each of the segments is located at the desired position. In one segment, the allowable moving range of the carriage may be from the minimum position to the maximum position. A set of moving allowable ranges of the carriage in these segments may form the allowable moving range set of the carriage in a corresponding field. Each carriage may include one moving allowable range set.

The left endpoint $A_i$ of the allowable moving range set of the left carriage may represent a minimum moving allowable position of the left carriage when each of the leaves in the i-th segment is located at the desired position (hereinafter, the minimum moving allowable position is called a minimum position for brevity). The minimum position may be represented by the following formula (1):

$$A_i = \text{Max}\{A_{ij}\} \tag{1}$$

where a position $A_{ij}$ may represent a position at which the motor drives the left carriage to make the front end of the left carriage aligned with the rear end of the j-th leaf when the j-th leaf in the i-th segment is located at the corresponding desired position, j is from 1 to k2, and k2 is a number of leaves on the left carriage. For example, the left carriage 16 as shown in FIG. 1 has fourteen leaves respectively located at the corresponding desired position, from top to bottom, number 1, 2, 3, 4, . . . , 14. When the left carriage 16 is located at the minimum position, the front end of the left carriage 16 may be aligned with the rear end of the leaf 1.

The right endpoint $B_{ij}$ of the allowable moving range set of the left carriage may represent a maximum moving allowable position of the left carriage when each of the k2 number of leaves in the i-th segment is located at the desired position (hereinafter, the maximum moving allowable position is called a maximum position for brevity). The maximum position may be represented by the following formula (2):

$$B_i = \text{Min}\{B_{ij}\} \tag{2}$$

where a position $B_{ij}$ may represent a position at which the motor drives the left carriage to make the front end of the left carriage aligned with the front end of the j-th leaf when the j-th leaf in the i-th segment is located at the corresponding desired position, such as the front end of the left carriage and the front end of the j-th leaf are located at a same position in the moving direction. For example, when the left carriage 16 is located at the maximum position, the front end of the left carriage 16 may be aligned with the front end of the leaf 7.

The left endpoint $A_i$ of the allowable moving range set of the right carriage may be represented by the following formula (3):

$$A_i = \text{Max}\{A_{ij}\} \tag{3}$$

where a position $A_{ij}$ may represent a position at which the motor drives the right carriage to make the front end of the right carriage aligned with the front end of the j-th leaf when the j-th leaf in the i-th segment is located at the corresponding desired position, j is from 1 to k2, and k2 is a number of leaves on the right carriage. For example, the right carriage 16 as shown in FIG. 1 has fourteen leaves respectively located at the corresponding desired position, from top to bottom, number 1, 2, 3, 4, . . . , 14. When the right carriage is located at the minimum position, the front end of the right carriage may be aligned with the front end of the leaf 8.

The right endpoint $B_i$ of the allowable moving range set of the right carriage may be represented by the following formula (4):

$$B_i = \text{Min}\{B_{ij}\} \tag{4}$$

where a position $B_{ij}$ may represent a position at which the motor drives the right carriage to make the front end of the right carriage aligned with the rear end of the j-th leaf when the j-th leaf in the i-th segment is located at the corresponding desired position. For example, when the right carriage as shown in FIG. 1 is located at the maximum position, the front end of the right carriage may be aligned with the rear end of the leaf 14.

It shall be understood that the two carriages are located at their respective initial positions before movement. In addition, according to examples of the present disclosure, the minimum position $A_i$ of the left carriage in the i-th segment may correspond to a position of a rear end of a right-most leaf among the left carriage when each of the leaves is located at the desired position. The maximum position $B_i$ of the left carriage in the i-th segment may correspond to a position of a front end of a left-most leaf among the left carriage when each of the leaves is located at the desired position. The minimum position $A_i$ of the right carriage in the i-th segment may correspond to a position of a front end of a right-most leaf among the right carriage when each of the leaves is located at the desired position. The maximum position $B_i$ of the right carriage in the i-th segment may correspond to a position of a rear end of a left-most leaf among the right carriage when each of the leaves is located at the desired position.

At step S103, a respective position of the carriage in each of the segments is determined according to the allowable moving range set.

In some implementations, based on the allowable moving range set, a point having a minimum of sum of absolute values of distances from the point to each of the sub-sets in the allowable moving range set may be selected from the allowable moving range set as a reference point. In some examples, a sum of absolute values of distances from a particular position to each of the sub-sets in the allowable moving range set is called a total moving distance from the particular position to the allowable moving range set. A position that is closest to the reference point in a sub-set corresponding to each of the segments may be selected as an optimal position of the carriage in the segment. This process may appropriately reduce moving distance and the number of movements for the carriage and effectively reduce the position error caused by the movement, thereby ensuring the accuracy of the formed radiation field.

In some examples, step S103 of determining the respective position of the carriage in each of the segments includes the following steps S1031-S1032.

At step S1031, a reference point of the carriage is determined according to the allowable moving range set, where a total moving distance from the reference point to the allowable moving range set is the minimum.

According to an example, a point having a minimum of the total moving distance from the point to the allowable moving range set may be determined as a reference point of the carriage. Where, a total moving distance $D_n$ from a point in the n-th sub-set in the allowable moving range set to the allowable moving range set may be determined by the following formula (5), where n is from 1 to k1 and k1 is the number of segments. The formula (5) is as follows:

$$D_n = \sum_{i=1}^{k1} |P_i - R_n|, \quad (5)$$

where, $A_i \leq R_n \leq B_i$, i is from 1 to k1, k1 may represent a number of the segments, $R_n$ is a candidate reference point of the n-th sub-set, $P_i$ is a point in the i-th sub-set in the allowable moving range set and is closest to $R_n$. For example, $P_i$ is a lower limit $A_i$ of the i-th sub-set when $R_n$ is located on the left side of the i-th sub-set; $P_i$ is an upper limit of $B_i$ of the i-th sub-set when $R_n$ is located on the right side of the i-th sub-set; and $P_i$ is the candidate reference point $R_n$ when $R_n$ is located within the i-th sub-set.

Correspondingly, the reference point of the carriage may correspond to a point having a minimum of total moving distance in the allowable moving range set. The reference point may be determined by the following formula (6):

$$\text{Min}\{Dn\} = \min\left\{\sum_{i=1}^{k1} |P_i - R_n|\right\}. \quad (6)$$

Those skilled in the art shall be understood that a genetic algorithm, a particle swarm optimization algorithm or an ant colony algorithm may be adopted for obtaining the reference point.

At step S1032, an optimal position sequence of the carriage is obtained by taking a position that is closest to the reference point in each of the sub-sets as an optimal position of the carriage in the segment corresponding to the sub-set.

For each of the segments, a point in a sub-set corresponding to the segment that is closest to the reference point may be taken as the optimal position of the carriage in the segment. The optimal position of the carriage in each of the segments may constitute the optimal position sequence of the carriage. In this way, when controlling the movement of the carriage, the control may be carried out in accordance with the optimal position sequence, such that the carriage may be moved in the vicinity of the reference point, therefore the movement is relatively small.

According to examples of the present disclosure, it may be assumed that the candidate reference points exist at the endpoints of each of the sub-sets in the allowable moving range set. In this case, the endpoints of each of the sub-sets in the allowable moving range set may be traversed and total moving distances from each of the endpoints of each of the sub-sets to the allowable moving range set may be determined. The endpoint corresponding to the minimum of the total moving distance may be taken as the reference point. In this way, the reference point may be obtained by a limited calculation and the method is easy to be implemented. The argument process will be described in detail below with a specific example.

Figure 4:
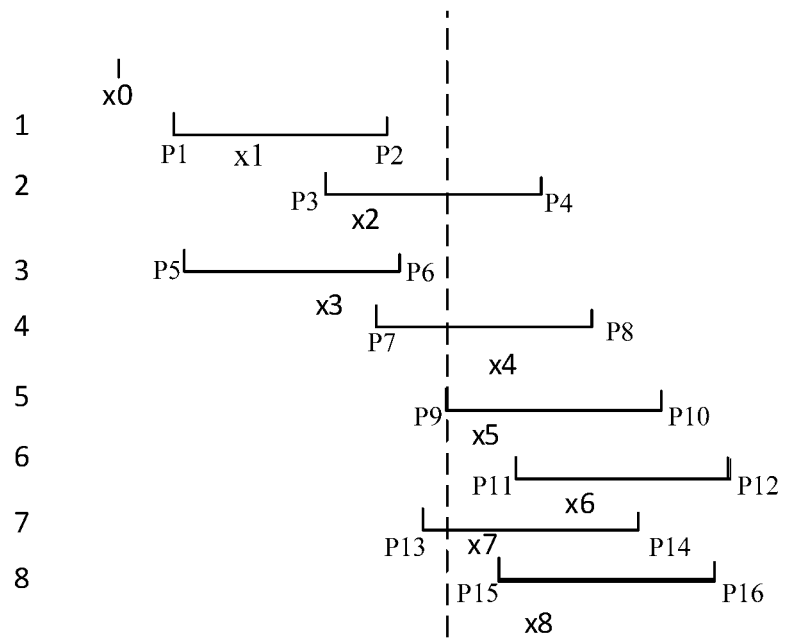
FIG. 4 is a schematic diagram illustrating an allowable moving range set of the carriage according to one or more examples of the present disclosure.

FIG. 4 is a diagram illustrating an allowable moving range set of the carriage according to an example of the present disclosure. As shown in FIG. 4, the allowable moving range set of the carriage totally includes eight sub-sets x1-x8, where x0 represents an initial position of the carriage. The reference point may be obtained according to the allowable moving range set and its possible position is divided by boundaries of each of the sub-sets. If there are t number of sub-sets, there will be 2t number of boundary points, which may divide 2t-1 intervals.

Figure 5:
FIG. 5 is a schematic diagram illustrating an endpoint division interval of an allowable moving range set according to one or more examples of the present disclosure.

FIG. 5 is a diagram illustrating an endpoint division interval of an allowable moving range set. As shown in FIG. 5, $X_{1A}$, $X_{2A}$, ... $X_{tA}$ respectively correspond to the left endpoints of the sub-sets x1, x2, ... xt, and $X_{1B}$, $X_{2B}$, ... $X_{tB}$ respectively correspond to the right endpoints of the sub-sets x1, x2, ..., xt. These endpoints may be considered to divide the allowable moving range set into 2t-1 intervals.

For convenience of recording, the endpoints are sequentially defined as $Z_1$, $Z_2$, $Z_3$, ..., $Z_{2t-1}$, $Z_{2t}$. Taking an endpoint in any one interval $F=[Z_n, Z_{n+1}]$, assuming that the allowable moving range set includes "a" number of sub-sets located on the left side of the interval F, "b" number of sub-sets located on the right side of the interval F and/or t-a-b number of sub-sets including the interval F. As can be seen, a point that is closest to the reference point is a right endpoint $X_{iB}$ of each of the sub-sets on the left side of the interval F; a point that is closest to the reference point is a left endpoint $X_{iA}$ of each of the sub-sets on the right side of the interval F; and a point that is closest to the reference point is a corresponding point of each of the sub-sets including the interval F and the minimum distance is zero. Thus, the formula (6) above may be equivalent to the following formula (7):

$$\text{Min}\left(\sum_{i=1}^{a} |X_{iB} - R| + \sum_{j=1}^{b} |X_{jA} - R|\right) = \text{Min}\left(aR - bR - \sum_{i=1}^{a} X_{iB} + \sum_{j=1}^{b} X_{jA}\right), \quad (7)$$

where, R represents a reference point and can be any point in the interval F. $X_{iB}$ is a point in each of the "a" number of intervals on the left side of the interval F and is closest to the reference point. $X_{iB}$ is a right endpoint of each of the "a" number of intervals on the left side of the interval F. $X_{iA}$ is a point in each of the "b" number of intervals on the right side of the interval F and is closest to the reference point. $X_{iA}$ is a left endpoint of each of the "b" number of intervals on the right side of the interval F. 2t-1 number of formulas may be obtained according to the 2t-1 number of intervals and the minimum value may be obtained according to the following formula (8):

$$\text{Min}\left\{\begin{array}{ll} a_1 R_1 - b_1 R_1 - \sum_{i=1}^{a_1} X_{iB} + \sum_{j=1}^{b_1} X_{jA} & R_1 \in [Z_1, Z_2] \\ a_2 R_2 - b_2 R_2 - \sum_{i=1}^{a_2} X_{iB} + \sum_{j=1}^{b_2} X_{jA} & R_2 \in [Z_2, Z_3] \\ \cdots & \\ a_{2t-1} R_{2t-1} - b_{2t-1} R_{2t-1} - & \\ \sum_{i=1}^{a_{2t-1}} X_{iB} + \sum_{j=1}^{b_{2t-1}} X_{jA} & R_{2t-1} \in [Z_{2t-1}, Z_{2t}] \end{array}\right\}. \quad (8)$$

Because each expression in the formula (8) is a first-order formula and has a boundary, it may be presumed the extremum value shall be at an endpoint, i.e., the optimal solution of the formula (8) shall appear at the endpoint. Therefore, if total moving distances from each endpoint of each of sub-sets in the allowable moving range set to the allowable moving range set are obtained and compared, it may be determined an endpoint having a minimum of total moving distance as the reference point.

Based on the above argument, in an example, step S103 of determining the respective position of the carriage in each of the segments according to the allowable moving range set can include the following steps S2031-S2033.

At step S2031, an endpoint of each of the sub-sets in the allowable moving range set is respectively taken as a hypothetical reference point, and a position sequence is obtained, where the position sequence includes a respective position point closest to the hypothetical reference point in each of the sub-sets.

At step S2032, a total moving distance from each of the hypothetical reference points to the allowable moving range set is respectively obtained. Where, the total moving distance from the hypothetical reference point to the allowable moving range set is a sum of absolute values of distances from the hypothetical reference point to each position point in the position sequence corresponding to the hypothetical reference point.

At step S2033, the hypothetical reference point having a minimum total moving distance among the obtained respective total moving distances is determined as a reference point of the carriage and the position sequence corresponding to the reference point is determined as an optimal position sequence of the carriage in the segment corresponding to the sub-set.

Each endpoint of the allowable moving range set may represent an endpoint of each of the sub-sets of the allowable moving range set. Each endpoint may be taken as a hypothetical reference point. When the carriage is located at the hypothetical reference point, a position sequence of the carriage may be obtained. The position sequence may be a set of position points for the carriage in each of the segments relative to the hypothetical reference point. The position sequence may include a position point that is closest to the hypothetical reference point in each of the sub-sets. All endpoints of the allowable moving range set may be traversed and the position sequence corresponding to each endpoint may be obtained, respectively. One position sequence is illustrated by taking FIG. 4 as an example, where a lower limit endpoint and an upper limit endpoint of each of the sub-sets x1-x8 are defined as [P1, P2], [P3, P4], . . . [P15, P16], respectively. Assuming that the lower limit endpoint P9 of the sub-set x5 is a hypothetical reference point, an endpoint in each of the sub-sets that is closest to the hypothetical reference point P9 is: the endpoint P2 of the sub-set x1, the endpoint P9 of the sub-set x2, the endpoint P6 of the sub-set x3, the endpoint P9 of the sub-set x4, the endpoint P9 of the sub-set x5, the endpoint P11 of the sub-set x6, the endpoint P9 of the sub-set x7, the endpoint P15 of the sub-set x8, respectively. The position sequence corresponding to the lower limit endpoint P9 of the sub-set x5 is {P2, P9, P6, P9, P9, P11, P9, P15}.

After that, the total moving distance from the endpoint of each of the sub-sets to the allowable moving range set may be respectively obtained, e.g., the sum of absolute values of distances from the endpoint of each of the sub-sets to each position point of the corresponding position sequence. An endpoint having the minimum total moving distance among the obtained total moving distances may be determined as a reference point of the carriage. The position sequence corresponding to the minimum total moving distance may be determined as the optimal position sequence of the carriage. In such a way, the reference point is determined from the endpoints of each of the sub-sets. The calculation is relatively small and the method is easy to be implemented.

In the examples above, it may be ensured that the carriage may be moved in the vicinity of the reference point in different segments. In this way, the movement of the carriage may be reduced and the position error caused by the movement may be reduced, thereby ensuring the accuracy of the formed radiation field.

Referring back to FIG. 3A, at step S104, the movement of the carriage is controlled according to the position of the carriage in each of segments.

When a treatment for a patient is performed, a static intensity modulated treatment mode or a dynamic intensity modulated treatment mode may be selected based on requirements. The movement of the carriage may be controlled in accordance with the determined position of the carriage in each of the segments.

In some implementations, before determining the position of the carriage in each of the segments, the following steps may be performed first: determining whether there is an intersection between each of the sub-sets with each other in the allowable moving range set; if there is the intersection, taking a position point that is closest to an initial position of the carriage in the intersection as a reference point and determining the reference point as the position of the carriage in each of the segments; and if there is no intersection, going to step S103.

The initial position of the carriage may refer to a position at which the carriage is located before first movement. In a case that there is an intersection between each of the sub-sets in the allowable moving range set, that is, each of the sub-sets has a common intersection or common moving range, the reference point may be determined in the intersection. The reference point may be a point that is closest to the initial position of the carriage in the intersection. Then the carriage may be kept at the position of the reference point in each of the segments and no movement of the carriage is performed. In this way, the movement of the carriage may be further reduced, it may be ensured that a desired shape in each of segments is formed by the leaves, and calculation for determining the reference point may be reduced. When there is no intersection between each of the sub-sets with each other in the allowable moving range set, the reference point may be determined according to the allowable moving range set, as noted above.

The method of controlling movement of a carriage of a multi-leaf collimator according to Example 1 of the present disclosure has been described in detail above. In this example, after the allowable moving range set of the carriage is obtained, a reference point may be determined from the allowable moving range set, where a sum of absolute values of distances from the reference point to each of the sub-sets in the allowable moving range set is a minimum. In this way, since the reference point is the position at which the carriage has the least movement in each of segments, the movement of the carriage in different segments is near the reference point, thereby effectively reducing the movement of the carriage and the position error caused by the movement, the accuracy of the formed radiation field may be ensured.

Example 2

Unlike Example 1, different movement strategies are adopted according to the allowable moving range set in Example 2, such that the carriage is fixed as far as possible, thereby reducing the movement of the carriage. The following will focus on description of different parts with the Example 1, and the same part will be omitted for brevity.

Figure 6:
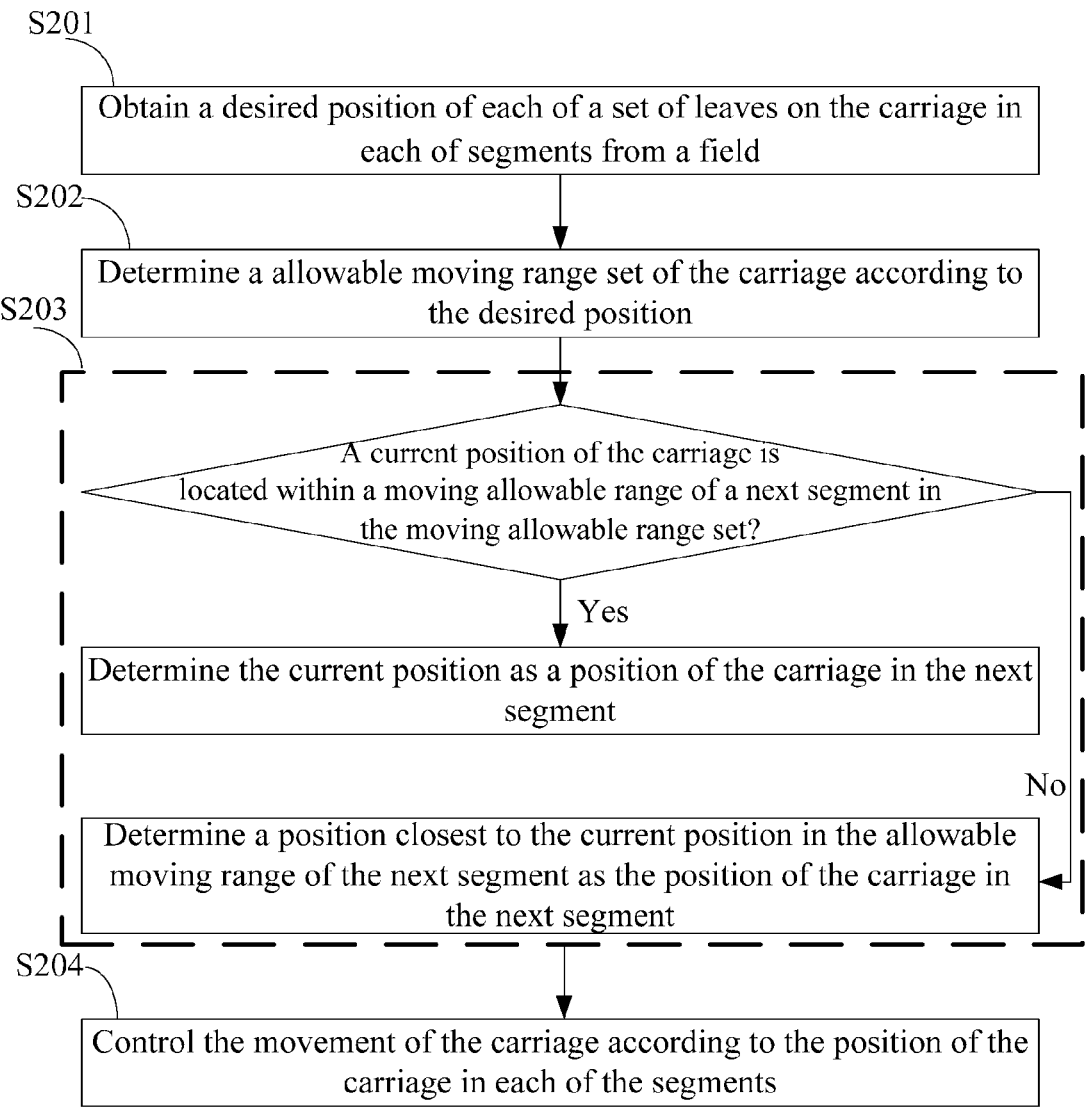
FIG. 6 is a flowchart illustrating a method of controlling movement of a carriage of a multi-leaf collimator according to Example 2 of the present disclosure.

FIG. 6 is a flowchart illustrating a method of controlling movement of a carriage of a multi-leaf collimator according to an example of the present disclosure. As shown in FIG. 6, at step S201, a desired position of each of a set of leaves on the carriage in each of segments in a field corresponding to a treatment plan is obtained. At step S202, an allowable moving range set of the carriage is determined according to the desired position. The steps S201 and S202 in Example 2 can be the same as the steps S101 and S102 in Example 1.

At step S203, a position of the carriage in each of the segments is determined according to the allowable moving range set.

In some implementations, determining the position of the carriage in each of the segments according to the allowable moving range set may include the following steps: determining whether a current position of the carriage is located within an allowable moving range of a next segment in the allowable moving range set; if yes, determining the current position as a position of the carriage in the next segment; and if no, determining a position closest to the current position in the allowable moving range of the next segment as the position of the carriage in the next segment.

According to an example, for two segments at adjacent moments, whether to change the position of the carriage in the next segment may be determined according to a relative position relationship between the allowable moving range of the carriage in the current segment and the allowable moving range of the carriage in the next segment. If it is necessary to change the position of the carriage in the next segment, the position of the carriage in the next segment may be changed to a position closest to the current position in the allowable moving range of the next segment. In this way, if the current position of the carriage is already located in the allowable moving range of the carriage in the next segment, the current position of the carriage may remain unchanged. In this way, there is no need to move the carriage again and the number of movements for the carriage may be further reduced. If the carriage is not located at the allowable moving range of the carriage in the next segment, the carriage in the next segment may be moved to a position that is closest to the current position in the allowable moving range of the next segment. In this way, when it is necessary to change the position of the carriage in the next segment, the movement distance of the carriage may be reduced as far as possible, the number of movements of the carriage may be reduced, and the position error caused by the movement may be reduced, thereby ensuring the accuracy of the formed radiation field.

At step S204, the movement of the carriage is controlled according to the position of the carriage in each of the segments. The step S204 shown in Example 2 is the same as the step S104 shown in Example 1.

The methods of controlling movement of a carriage of a multi-leaf collimator in examples of the present disclosure have been described in detail above. To verify the effect of the movement control methods in examples of the present disclosure, the following simulation tests were performed. In the simulation tests, the method shown in the Example 1, the method shown in the Example 2 and an "Average Difference Value method" were adopted for determining the position of the carriage, respectively. Determining the position of the carriage according to the Average Difference Value method means that an average value of the difference between the desired position of each of the set of leaves on the carriage and the actual current position of each of the set of leaves on the carriage may be used as a relative position of the carriage. For three groups of static intensity modulated treatment prescription, the position of the carriage may be determined according to the movement control method of Example 1, Example 2 and Average Difference Value method. Corresponding experimental data may be shown in Table 1, Table 2, and Table 3, respectively.

TABLE 1

Verified Data Sheet for First Treatment Prescription

| Method | Surface A/B | Actual Moving allowable Distance (mm) | Fluctuation Parameter (mm) | Number of Movements | Whether to meet beam condition |
|---|---|---|---|---|---|
| Example 1 | A | 159.4 | 18.93 | 6 | Yes |
| Example 2 | A | 159.4 | 48.36 | 17 | Yes |
| Average Difference Value method | A | 156.1 | 38.38 | 27 | No |
| Example 1 | B | 233.1 | 25.33 | 7 | Yes |
| Example 2 | B | 233.1 | 26.86 | 8 | Yes |
| Average Difference Value method | B | 313.6 | 42.79 | 27 | No |

TABLE 2

Verified Data Sheet for Second Treatment Prescription

| Method | Surface A/B | Actual Moving allowable Distance (mm) | Fluctuation Parameter (mm) | Number of Movements | Whether to meet beam condition |
|---|---|---|---|---|---|
| Example 1 | A | 139.3 | 15.49 | 7 | Yes |
| Example 2 | A | 139.3 | 42.19 | 31 | Yes |
| Average Difference Value method | A | 145.3 | 30.09 | 33 | Yes |
| Example 1 | B | 166.5 | 18.09 | 11 | Yes |
| Example 2 | B | 166.5 | 18.72 | 12 | Yes |

TABLE 2-continued

Verified Data Sheet for Second Treatment Prescription

| Method | Surface A/B | Actual Moving allowable Distance (mm) | Fluctuation Parameter (mm) | Number of Movements | Whether to meet beam condition |
|---|---|---|---|---|---|
| Average Difference Value method | B | 294.5 | 33.39 | 33 | No |

TABLE 3

Verified Data Sheet for Third Treatment Prescription

| Method | Surface A/B | Actual Moving allowable Distance (mm) | Fluctuation Parameter (mm) | Number of Movements | Whether to meet beam condition |
|---|---|---|---|---|---|
| Example 1 | A | 105.7 | 17.77 | 3 | Yes |
| Example 2 | A | 105.7 | 27.39 | 13 | Yes |
| Average Difference Value method | A | 124.3 | 29.90 | 13 | Yes |
| Example 1 | B | 170.1 | 30.17 | 2 | Yes |
| Example 2 | B | 170.1 | 31.01 | 5 | Yes |
| Average Difference Value method | B | 322.9 | 44.43 | 13 | Yes |

The surfaces A and B in the three tables may refer to one side of carriage that carries a set of leaves in the multi-leaf collimator and the other side of carriage that carries another set of leaves in the multi-leaf collimator, respectively. The number of movements may represent a total number of movements for the carriage throughout the treatment prescription. The actual moving allowable distance may represent a total distance of movements for the carriage throughout the treatment prescription. The fluctuation parameter may represent a square root value of the square sum of distances between the position of the carriage in each of the segments and the reference point. In the Example 1, the reference point is determined from the moving allowable range set. However, in the Example 2 and the Average Difference Value method, the movement of the carriage in the next segment is based on the position of the carriage in the current segment, and thus the reference point may be the position point of the carriage in the current segment when the current position point is within the moving allowable range of the next segment.

As can be seen from the test results shown in the above-described Table 1, Table 2 and Table 3, Example 1 and Example 2 of the present disclosure satisfy the beam condition, but Average Difference Value method does not satisfy the beam condition in some cases. In addition, by comparing the movement control method of Example 1 and the movement control method of Example 2 with Average Difference Value method, the number of movements and the actual allowable moving distance in Example 1 and Example 2 are less than those in Average Difference Value method. The number of movements and the actual allowable moving distance in Example 1 are further reduced, and the fluctuation range in Example 1 is further reduced, which is more advantageous in practical application to reduce error caused by a plurality of movements and large range of movement, thereby improving the accuracy of system and treatment effect.

Figure 7:
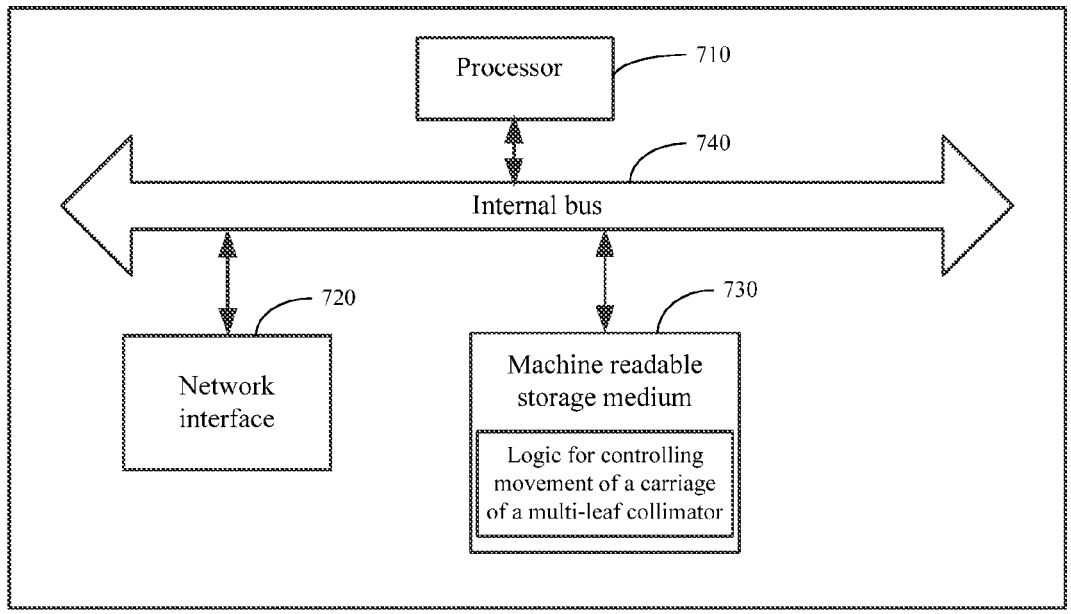
FIG. 7 is a hardware architecture diagram of a device for controlling movement of a carriage of a multi-leaf collimator according to one or more examples of the present disclosure.

A device for controlling movement of a carriage of a multi-leaf collimator is provided in the present disclosure, where the device may be implemented by software, or may be implemented by a combination of hardware and/or software. FIG. 7 is a hardware architecture diagram of a device for controlling movement of a carriage of a multi-leaf collimator according to one or more examples of the present disclosure. The device shown in FIG. 7 may include a processor 710, a network interface 720, a machine readable storage medium 730 and an internal bus 740. Besides the processor 710, the communications interface 720, the machine readable storage medium 730 and the internal bus 740, the device may further include other hardware based on actual functions, and detailed description is omitted for brevity.

In different examples, the machine readable storage medium 730 may be Read-Only Memory (ROM), Random Access Memory (RAM), volatile memory, non-volatile memory, flash memory, storage drives (such as, a hard drive), solid state drive, any type of storage disks (such as, CD-ROM, DVD, etc.), or similar storage medium, or a combination thereof.

Figure 8:
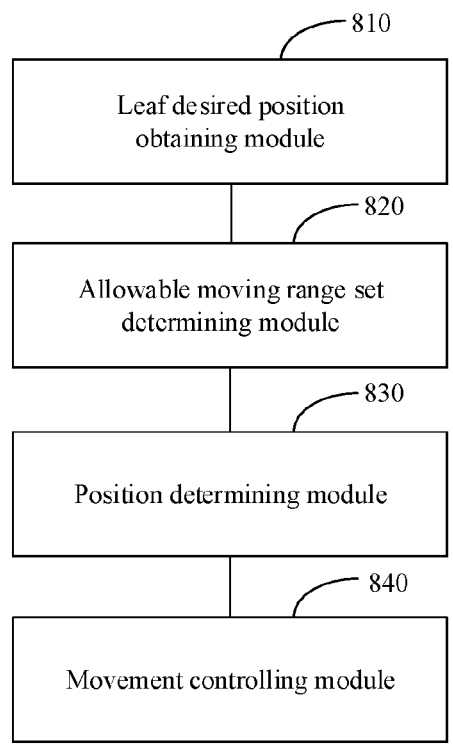
FIG. 8 is a block diagram of a logic for controlling movement of a carriage of a multi-leaf collimator according to one or more examples of the present disclosure.

In an example, machine readable instructions corresponding to a logic for controlling movement of a carriage of a multi-leaf collimator are stored in the machine readable storage medium 730. FIG. 8 is a block diagram of a logic for controlling movement of a carriage of a multi-leaf collimator according to one or more examples of the present disclosure. Divided by functions, the logic for controlling movement of a carriage of a multi-leaf collimator may include a leaf desired position obtaining module 810, an allowable moving range set determining module 820, a position determining module 830, and a movement controlling module 840.

The leaf desired position obtaining module 810 may be configured to obtain a desired position of each of a set of leaves on the carriage in each of segments from a field.

The allowable moving range set determining module 820 may be configured to determine an allowable moving range of the carriage according to the desired position, where the allowable moving range set includes an allowable moving range of the carriage in each of the segments.

The position determining module 830 may be configured to determine a respective position of the carriage in each of the segments according to the allowable moving range set.

The movement controlling module 840 may be configured to control a movement of the carriage according to the position of the carriage in each of the segments.

In some examples, the position determining module 830 may further include a determining sub-module and a position determining sub-module.

The determining sub-module may be configured to determine whether a current position of the carriage is located within an allowable moving range of a next segment in the allowable moving range set.

The position determining sub-module may be configured to determine the current position as a position of the carriage in the next segment when the determining sub-module determines that the current position of the carriage is located within the allowable moving range of the next segment; and may be configured to determine a position closest to the current position in the allowable moving range of the next segment as the position of the carriage in the next segment when the determining sub-module determines that the current position of carriage is out of the allowable moving range of the next segment.

In another example, the position determining module 830 may further include a reference point determining sub-module, an optimal position sequence obtaining sub-module and an optimal position determining sub-module.

The reference point determining sub-module may be configured to determine a reference point of the carriage according to the allowable moving range set, where a total moving distance from the reference point to the allowable moving range set is a minimum and the total moving distance represents a sum of absolute values of distances for the carriage from the reference point to each of the allowable moving ranges in the allowable moving range set.

The optimal position sequence obtaining sub-module may be configured to generate an optimal position sequence of the carriage by taking a position that is closest to the reference point in each of the allowable moving ranges as an optimal position of the carriage in the allowable moving range.

The optimal position determining sub-module may be configured to determine the position of the carriage in each of the segments according to the optimal position sequence.

When calculating a minimum of the sum of distances from the endpoints of each of the allowable moving ranges to each of the allowable moving ranges, the endpoint having the minimum of the sum may be taken as the reference point, where the calculating method may be referred to the above Example 1. For example, the distance from one endpoint of one moving allowable range to each of the allowable moving ranges may be a distance from said endpoint to an endpoint of each of the allowable moving ranges that is closest to said endpoint.

In another example, the position determining module 830 may further include a position sequence obtaining sub-module and a reference point and optimal position sequence determining sub-module.

The position sequence obtaining sub-module may be configured to take an endpoint of each of the allowable moving ranges in the allowable moving range set as a hypothetical reference point and obtain a position sequence when the carriage is located at the hypothetical reference point, where the position sequence includes a position point that is closest to the hypothetical reference point in each of the allowable moving ranges.

The reference point and optimal position sequence determining sub-module may be configured to respectively obtain a total moving distance from each of the hypothetical reference points to the allowable moving range set, where the total moving distance represents a sum of absolute values of distances for the carriage from the hypothetical reference point to each of position points in the position sequence corresponding to the hypothetical reference point; take the hypothetical reference point having a minimum of total moving distance as a reference point of the carriage; and determine the position of the carriage in each of the segments according to a position sequence corresponding to the reference point.

In another example, the position determining module 830 may further include an allowable moving range set intersection determining sub-module The allowable moving range set intersection determining sub-module may be configured to determine whether there is an intersection between each of the allowable moving ranges with each other in the allowable moving range set. If there is the intersection, a position point that is closest to an initial position of the carriage in the intersection may be taken as a reference point and the reference point may be determined as the position of the carriage in each of the segments. If there is no intersection, the position of the carriage in each of the segments may be determined according to the allowable moving range set.

The example below may be implemented with software, which may further describe how the device for controlling movement of a carriage of a multi-leaf collimator runs the logic. In an example, the logic for controlling movement of the carriage of the multi-leaf collimator in the present disclosure should be understood as machine readable instructions stored in the machine readable storage medium 730. When the processor 710 of the device for controlling movement of a carriage of a multi-leaf collimator executes the logic, the processor 710 executes corresponding machine readable instructions of the logic stored in the machine readable storage medium 730 to:

obtain a desired position of each of a set of leaves on the carriage in each of segments from a field;

determine an allowable moving range of the carriage according to the desired position, wherein the allowable moving range set comprises an allowable moving range of the carriage in each of the segments;

determine a respective position of the carriage in each of the segments according to the allowable moving range set; and control a movement of the carriage according to the position of the carriage in each of the segments.

According to an example, when determining a position of the carriage in each of the segments according to the allowable moving range set, said machine readable instructions further cause the processor 710 to:

determine a reference point of the carriage according to the allowable moving range set, wherein a total moving distance from the reference point to the allowable moving range set is a minimum and the total moving distance represents a sum of absolute values of distances for the carriage from the reference point to each of the allowable moving ranges in the allowable moving range set; and take a position that is closest to the reference point in each of the allowable moving ranges as the position of the carriage in the corresponding segment.

According to another example, when determining a position of the carriage in each of the segments according to the allowable moving range set, said machine readable instructions further cause the processor 710 to:

take an endpoint of each of the allowable moving ranges in the allowable moving range set as a hypothetical reference point;

obtain a position sequence when the carriage is located at the hypothetical reference point, wherein the position sequence comprises a position point that is closest to the hypothetical reference point in each of the allowable moving ranges;

respectively obtain a total moving distance from each of the hypothetical reference points to the allowable moving range set, where the total moving distance represents a sum of absolute values of distances for the carriage from the hypothetical reference point to each of position points in the position sequence corresponding to the hypothetical reference point;

take the hypothetical reference point having a minimum of the total moving distance as a reference point of the carriage; and;

determine the position of the carriage in each of the segments according to a position sequence corresponding to the reference point.

According to another example, the machine readable instructions further cause the processor 710 to:

determine whether there is an intersection existed between each of the allowable moving ranges with each other in the allowable moving range set;

if there is the intersection between each of the allowable moving ranges with each other, take a position point that is closest to an initial position of the carriage in the intersection as a reference point, and determine the reference point as the position of the carriage in each of the segments; and if there is no intersection between each of the allowable moving ranges with each other, determine the position of the carriage in each of the segments according to the allowable moving range set.

According to another example, when determining a position of the carriage in each of the segments according to the allowable moving range set, said machine readable instructions further cause the processor 710 to:

determine whether a current position of the carriage is located within an allowable moving range of a next segment in the allowable moving range set;

determine the current position as a position of the carriage in the next segment if the current position of carriage is located within the allowable moving range of the next segment; and determine a position closest to the current position in the allowable moving range of the next segment as the position of the carriage in the next segment if the current position of carriage is not located within the allowable moving range of the next segment.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

For simplicity and illustrative purposes, the present disclosure is described by referring mainly to examples thereof. In the above description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of controlling movement of a carriage of a multi-leaf collimator, comprising:

obtaining a desired position of each of a set of leaves on the carriage in each of a plurality of segments from a field based on a treatment prescription, wherein the treatment prescription includes a treatment plan corresponding to the field, and each of the segments corresponds to a radiation field for rays to pass through which is formed when each of the set of leaves is located at the desired position at a respective time of the treatment plan;

determining an allowable moving range set of the carriage according to the desired position, wherein the allowable moving range set comprises a respective allowable moving range of the carriage in each of the segments;

determining a respective position of the carriage in each of the segments according to the allowable moving range set; and controlling the movement of the carriage according to the determined respective positions of the carriage in the segments, wherein determining the allowable moving range set of the carriage comprises:

determining, for each of the segments, endpoints of the respective allowable moving range of the carriage, wherein the endpoints represent minimum and maximum positions of the carriage when the leaves are in the desired positions in the segment and an end of the carriage is aligned with ends of the leaves.

2. The method according to claim 1, wherein determining the respective position of the carriage in each of the segments according to the allowable moving range set comprises:
   determining a reference point according to the allowable moving range set; and
   taking a position closest to the reference point in each of the allowable moving ranges as the respective position of the carriage in the corresponding segment.

3. The method according to claim 2, wherein determining the reference point according to the allowable moving range set comprises:
   calculating, for each of a plurality of candidate reference points, a respective total moving distance representing a sum of absolute values of distances for the carriage from the candidate reference point to each of the allowable moving ranges in the allowable moving range set; and
   determining the candidate reference point having a minimum total moving distance among the determined respective total moving distances to be the reference point.

4. The method according to claim 3, further comprising determining a distance for the carriage from the candidate reference point to each of the allowable moving ranges by
   determining the distance to be zero if the candidate reference point is within an allowable moving range, and
   determining the distance to be from the candidate reference point to a closest endpoint of an allowable moving range if the candidate reference point is out of the allowable moving range.

5. The method according to claim 1, wherein determining the respective position of the carriage in each of the segments according to the allowable moving range set comprises:
   taking an endpoint of each of the allowable moving ranges in the allowable moving range set as a hypothetical reference point;
   generating, for each of the hypothetical reference points, a corresponding position sequence including a respective position point closest to the hypothetical reference point in each of the allowable moving ranges;
   calculating, for each of the hypothetical reference points, a respective total moving distance representing a sum of absolute values of distances for the carriage from the hypothetical reference point to each of the position points in the corresponding position sequence;
   determining the hypothetical reference point with a minimum total moving distance among the calculated respective total moving distances to be a reference point of the carriage; and
   determining the respective position of the carriage in each of the segments according to a position sequence corresponding to the reference point.

6. The method according to claim 1, further comprising:
   determining whether there is an intersection between each of the allowable moving ranges in the allowable moving range set;
   in response to determining that there is an intersection between each of the allowable moving ranges, taking a position point closest to an initial position of the carriage in the intersection as a reference point, and determining the reference point as the position of the carriage in each of the segments; and
   in response to determining that there is no intersection between each of the allowable moving ranges, determining the respective position of the carriage in each of the segments according to the allowable moving range set.

7. The method according to claim 1, wherein determining the respective position of the carriage in each of the segments according to the allowable moving range set comprises:
   determining whether a current position of the carriage is located within an allowable moving range of a next segment in the allowable moving range set;
   in response to determining that the current position of the carriage is located within the allowable moving range of the next segment, determining the current position to be the respective position of the carriage in the next segment; and
   in response to determining that the current position of the carriage is out of the allowable moving range of the next segment, determining a position closest to the current position in the allowable moving range of the next segment is to be the respective position of the carriage in the next segment.

8. The method according to claim 1, wherein controlling the movement of the carriage comprises:
   jointly moving the carriage and the set of leaves on the carriage.

9. A device for controlling movement of a carriage of a multi-leaf collimator, comprising:
   one or more processors; and
   a non-transitory machine-readable storage medium having instructions stored thereon which, when executed by the one or more processors, cause the one or more processors to perform operations comprising:
      obtaining a desired position of each of a set of leaves on the carriage in each of a plurality of segments from a field based on a treatment prescription, wherein the treatment prescription includes a treatment plan corresponding to the field, and each of the segments corresponds to a radiation field formed when each of the set of leaves is located at the desired position at a respective time of the treatment plan;
      determining an allowable moving range set of the carriage according to the desired position, wherein the allowable moving range set comprises a respective allowable moving range of the carriage in each of the segments;
      determining a respective position of the carriage in each of the segments according to the allowable moving range set; and
      controlling the movement of the carriage according to the determined respective positions of the carriage in the segments,
   wherein determining the allowable moving range set of the carriage comprises:
      determining, for each of the segments, endpoints of the respective allowable moving range of the carriage, wherein the endpoints represent minimum and maximum positions of the carriage when the leaves are in the desired positions in the segment and an end of the carriage is aligned with ends of the leaves.

10. The device according to claim 9, wherein determining the respective position of the carriage in each of the segments according to the allowable moving range set comprises:
   determining a reference point according to the allowable moving range set; and taking a position closest to the reference point in each of the allowable moving ranges as the respective position of the carriage in the corresponding segment.

11. The device according to claim 10, wherein determining the reference point according to the allowable moving range set comprises:
    calculating, for each of a plurality of candidate reference points, a respective total moving distance representing a sum of absolute values of distances for the carriage from the candidate reference point to each of the allowable moving ranges in the allowable moving range set; and
    determining the candidate reference point having a minimum total moving distance among the determined respective total moving distances to be the reference point.

12. The device according to claim 11, wherein the operations further comprise:
    determining a distance for the carriage from the candidate reference point to each of the allowable moving ranges by
        determining the distance to be zero if the candidate reference point is within an allowable moving range, and
        determining the distance to be from the candidate reference point to a closest endpoint of an allowable moving range if the candidate reference point is out of the allowable moving range.

13. The device according to claim 9, wherein determining the respective position of the carriage in each of the segments according to the allowable moving range set comprises:
    taking an endpoint of each of the allowable moving ranges in the allowable moving range set as a hypothetical reference point;
    generating, for each of the hypothetical reference points, a corresponding position sequence including a respective position point closest to the hypothetical reference point in each of the allowable moving ranges;
    calculating, for each of the hypothetical reference points, a respective total moving distance representing a sum of absolute values of distances for the carriage from the hypothetical reference point to each of the position points in the corresponding position sequence;
    determining the hypothetical reference point with a minimum total moving distance among the calculated respective total moving distances to be a reference point of the carriage; and
    determining the respective position of the carriage in each of the segments according to a position sequence corresponding to the reference point.

14. The device according to claim 9, wherein the operations further comprise:
    determining whether there is an intersection between each of the allowable moving ranges in the allowable moving range set;
    in response to determining that there is an intersection between each of the allowable moving ranges, taking a position point closest to an initial position of the carriage in the intersection as a reference point, and determining the reference point as the position of the carriage in each of the segments; and
    in response to determining that there is no intersection between each of the allowable moving ranges, determining the respective position of the carriage in each of the segments according to the allowable moving range set.

15. The device according to claim 9, wherein determining the respective position of the carriage in each of the segments according to the allowable moving range set comprises:
    determining whether a current position of the carriage is located within an allowable moving range of a next segment in the allowable moving range set;
    in response to determining that the current position of the carriage is located within the allowable moving range of the next segment, determining the current position to be the respective position of the carriage in the next segment; and
    in response to determining that the current position of the carriage is out of the allowable moving range of the next segment, determining a position closest to the current position in the allowable moving range of the next segment is to be the respective position of the carriage in the next segment.

16. The device according to claim 9, wherein controlling the movement of the carriage comprises:
    jointly moving the carriage and the set of leaves on the carriage.

* * * * *